United States Patent
Teague et al.

(10) Patent No.: US 8,366,754 B2
(45) Date of Patent: Feb. 5, 2013

(54) BI-DIRECTIONALLY EXPANDABLE STERNAL CLAMP DEVICE

(75) Inventors: Michael Teague, Ponte Vedra Beach, FL (US); Shawn Burke, Jacksonville, FL (US); Thomas S. Johnston, Jacksonville, FL (US)

(73) Assignee: KLS-Martin, L.P., Jacksonville, FL (US)

( * ) Notice: Subject to any disclaimer, the term of this patent is extended or adjusted under 35 U.S.C. 154(b) by 727 days.

(21) Appl. No.: 12/290,604

(22) Filed: Oct. 31, 2008

(65) Prior Publication Data

US 2009/0138054 A1  May 28, 2009

Related U.S. Application Data

(60) Provisional application No. 61/001,628, filed on Nov. 2, 2007.

(51) Int. Cl.
| | |
|---|---|
| A61F 2/08 | (2006.01) |
| A61B 17/04 | (2006.01) |
| A61B 17/84 | (2006.01) |
| A61B 1/32 | (2006.01) |
| A44B 1/04 | (2006.01) |
| A44B 11/25 | (2006.01) |
| A44B 13/00 | (2006.01) |
| A44B 17/00 | (2006.01) |

(52) U.S. Cl. ........ 606/324; 606/905; 600/231; 600/233; 24/372

(58) Field of Classification Search .............. 606/57, 606/213, 216, 324, 282, 328, 905; 600/231, 600/233; 24/309, 329, 372, 522

See application file for complete search history.

(56) References Cited

U.S. PATENT DOCUMENTS

| | | | |
|---|---|---|---|
| 3,473,528 A | 10/1969 | Mishkin et al. | |
| 4,201,215 A | 5/1980 | Crossett et al. | |
| 4,279,248 A | 7/1981 | Gabbay | |
| 4,583,541 A | 4/1986 | Barry | |
| 4,815,455 A * | 3/1989 | Kim | 606/57 |
| 5,139,498 A | 8/1992 | Astudillo Ley | |
| 5,196,012 A * | 3/1993 | Malka | 606/54 |
| 5,246,443 A * | 9/1993 | Mai | 606/78 |
| 5,667,481 A * | 9/1997 | Villalta et al. | 600/224 |
| 5,944,658 A * | 8/1999 | Koros et al. | 600/232 |
| 6,051,007 A | 4/2000 | Hogendijk et al. | |
| 6,217,580 B1 | 4/2001 | Levin | |
| 6,302,899 B1 | 10/2001 | Johnson et al. | |
| 6,540,769 B1 * | 4/2003 | Miller, III | 606/216 |
| 6,712,821 B2 | 3/2004 | Gabbay | |
| 6,746,396 B1 * | 6/2004 | Segermark et al. | 600/233 |
| 7,033,377 B2 * | 4/2006 | Miller, III | 606/213 |
| 7,377,472 B2 * | 5/2008 | Brown et al. | 248/74.1 |
| 7,887,482 B2 * | 2/2011 | Hamada | 600/233 |
| 2005/0159651 A1* | 7/2005 | Raymond et al. | 600/213 |
| 2007/0043371 A1* | 2/2007 | Teague et al. | 606/71 |
| 2007/0156025 A1* | 7/2007 | Marchek et al. | 600/224 |

* cited by examiner

*Primary Examiner* — Kevin T Truong
*Assistant Examiner* — David Bates
(74) *Attorney, Agent, or Firm* — Thomas C. Saitta; Stephen E. Kelly; Rogers Towers, P.A.

(57) ABSTRACT

A sizable sternal closure clamp device for securing and retaining longitudinally or transversely divided halves of a sternum, the device having four body members and four engagement members that are positioned in inter-rib spaces on both sides of the sternum. The body members are interconnected in a sliding or telescoping manner that allows the device to be expanded or contracted in two orthogonal directions.

20 Claims, 1 Drawing Sheet

BI-DIRECTIONALLY EXPANDABLE STERNAL CLAMP DEVICE

This patent application claims the benefit of U.S. Provisional Patent Application Ser. No. 61/001,628, filed Nov. 2, 2007.

BACKGROUND OF THE INVENTION

This invention generally relates to devices used to rejoin a human sternum that has been severed longitudinally, and more particularly relates to such devices that function in a clamping manner to retain the severed sternum portions in a closed and abutting relationship post-operatively.

It is often necessary in surgical operations to longitudinally sever the patient's sternum so that the ribs may be spread to provide access to internal organs such as the heart. It is then necessary to secure the sternum halves together for post-operative recovery. Various closure techniques are used to accomplish this task. For example, holes may be drilled into the sternum halves and suture material passed through and tightened to cinch the sternum halves together. Apertured plates may be added to further rigidify the sternum post-operatively, with the suture material being passed through the apertures in the plate and the sternum. Encircling members may be wrapped around the sternum and tightened. Toothed bridging members extending across the cut line may be pressed into the sternum surfaces and/or secured with threaded rods extending between the sternal halves.

Another sternal closure technique involves the use of clamps having hook-like projections or engagement members on both ends, the clamp being positioned laterally relative to the sternal incision with the projections being disposed between adjoining rib pairs. The clamp is then linearly contracted or compressed to shorten the device and force the sternal halves together, the clamp typically comprising two members joined in a linear telescoping manner. Locking or securing means, either permanent or releasable, maintain the clamp in the contracted configuration.

Often the sternum may be in a weakened state, in which case the sternal clamps having a pairs of engagement members on each side are utilized in order to spread the compressive forces, with the engagement members on a given side of the sternum being disposed to either side of a rib. A problem with this design is that size of the rib the distance between adjacent ribs will vary, and thus the separation distance between the two engagement members may not be correct to properly locate the sternal clamp.

Examples of such techniques and sternal clamp devices are described in U.S. Pat. No. 3,473,528 to Mishkin et al., U.S. Pat. No. 4,201,215 to Crossett et al., U.S. Pat. No. 4,279,248 to Gabbay, U.S. Pat. No. 4,583,541 to Barry, U.S. Pat. No. 5,139,498 to Astudillo Ley, U.S. Pat. No. 6,051,007 to Hogendijk et al., U.S. Pat. No. 6,217,580 to Levin, U.S. Pat. No. 6,302,899 to Johnson et al., U.S. Pat. No. 6,540,769 to Miller, III, and U.S. Pat. No. 6,712,821 to Gabbay.

It is an object of this invention to provide a bi-directionally expandable sternal closure clamp device having the functionality of a contractible sternal clamp, such that the sternal halves may be quickly and easily pressed or drawn together in a sliding or telescoping manner and retained in position, but which also is extendible in the direction parallel to the sternal incision, such that the engagement members on each side of the sternum can be properly spaced to surround single or multiple ribs.

SUMMARY OF THE INVENTION

The invention is in general a sternal closure clamp device for post-operatively closing, securing and supporting a patient's sternum that has been longitudinally severed into two sternal halves. The sternal clamp generally comprises four interconnected body members that together form a unified, bi-directionally expandable clamp, with four engagement members that extend generally from the area of the corners of the unified clamp, such that two engagement members are disposed on one side and two engagement members are disposed on the other side. The engagement members are means to engage, secure or otherwise retain the sternal halves in an abutting relationship, with the engagement members comprising hooks, projections, fingers or the like, whereby the engagement members can be disposed against the outer edges of the sternal halves and between adjoining ribs, with the two engagement members located on a given side being positioned in the inter-rib spaces to either side of a single rib or multiple ribs when the clamp is extended. The clamp is also extendable in the sternal longitudinal direction, such that the spacing between engagement members on each side can be adjusted to account for variations in rib size.

The body members interconnect in a sliding or telescopic manner and are relatively adjustable, such that the distance between the engagement members can be lengthened in the longitudinal direction relative to the sternum to properly locate the engagement members in to the inter-rib spaces, then shortened in the transverse direction to press or draw the sternal halves together. The sternal clamp further comprises locking means to secure and retain the body members in the contracted position, with the locking means preferably being releasable.

DETAILED DESCRIPTION OF THE INVENTION

With reference to the drawings, the invention will now be described in detail with regard for the best mode and the preferred embodiment. The invention is a sternal closure clamp device used to close, secure and support a sternum post-operatively, the sternum having been severed longitudinally into left and right lateral sternal halves to provide access to the interior of the chest, wherein the clamp may be extended both laterally and longitudinally relative to the sternal incision.

In general, the invention is a sternal clamp 10 having means to expand and contract the clamp 10 in a first direction longitudinally relative to the sternum, means to expand and contract the clamp 10 in a second direction orthogonal to the first direction and transverse relative to the sternum, and means to engage the sides of the sternum and alternatively the sides of ribs such that halves of a longitudinally divided sternum can be compressed together and held in place during healing and such that the halves of a transversely divided sternum can be compressed and held together during healing.

Figure 1:
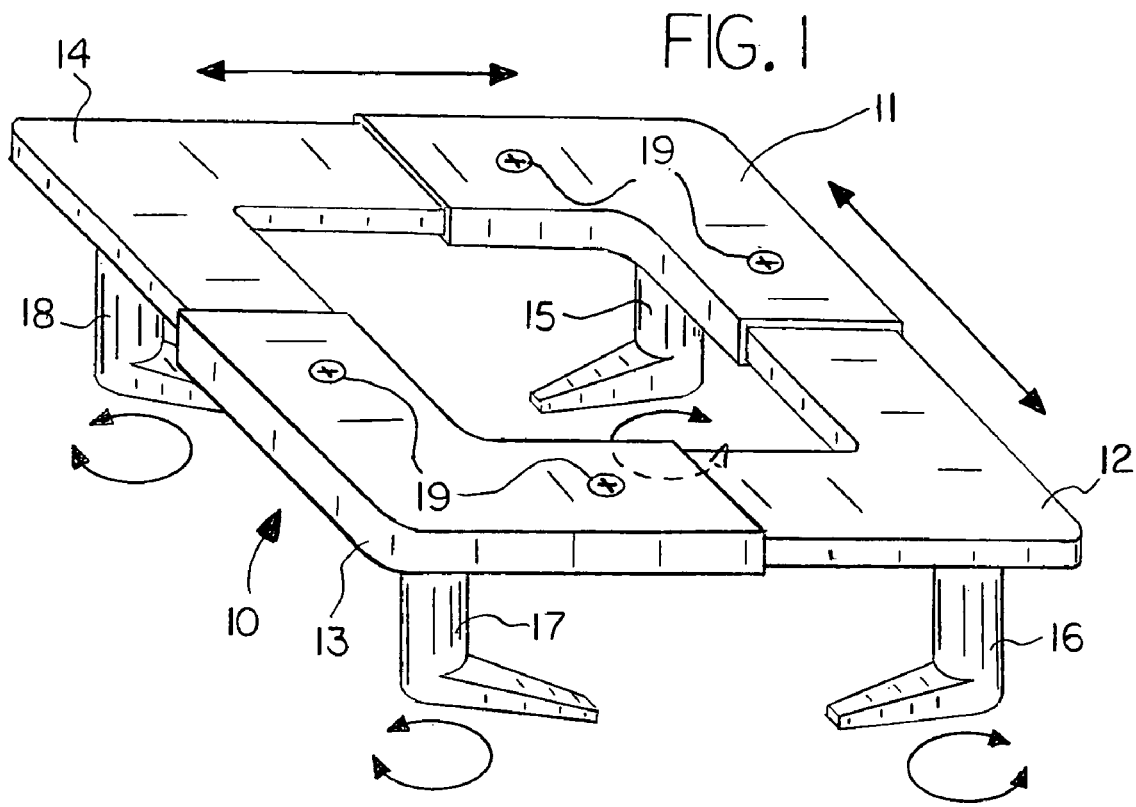
FIG. 1 is a perspective view of an embodiment of the sternal clamp.

In one embodiment of the device, as shown in FIG. 1, the sternal clamp 10 comprises four, generally L-shaped, telescopically interconnected body members 11, 12, 13 and 14 that in combination form a bi-directionally expandable clamp 10, with four engagement members 15, 16, 17 and 18 that extend generally from the area of the corners of the assembled clamp 10, with two engagement members 15 and 16 disposed on one side of the clamp 10 and two engagement members 17 and 18 disposed on the other side of the clamp 10. The engagement members 15, 16, 17 and 18 are means to engage, secure or otherwise retain the sternal halves or the ribs in an abutting relationship, with the engagement members 15, 16, 17 and 18 having hooks, projections, fingers or the like disposed on their ends, whereby the engagement members 15, 16, 17 and 18 are disposed against the outer edges of the sternal halves and between adjoining ribs, with the two paired engagement members 15/16 and 17/18 on a given side being positioned in the inter-rib spaces to either side of a single rib or multiple ribs when the clamp 10 is extended. Prior to positioning of the engagement members 15, 16, 17 and 18, the clamp 10 is contracted or extended in the sternal longitudinal direction in order to decrease or increase the distance between engagement members 15 and 16 and engagement members 17 and 18 to account for variations in rib spacing. The engagement members 15, 16, 17 and 18 are mounted to the body members 11, 12, 13 and 14 in a manner that allows each to be rotated such that the engagement members on a given side may be pointed towards each other in order to abut the sides of ribs or pointed across the clamp toward the engagement members on the other side in order to engage the sternal halves.

The body members 11, 12, 13 and 14 interconnect in a sliding or telescopic manner and are relatively adjustable, such that the distance between the engagement members 15, 16, 17 and 18 can be lengthened in two orthogonal directions to properly locate the engagement members 15, 16, 17 and 18 relative to the inter-rib spaces, then shortened in the transverse direction to press or draw the sternal halves together. In the embodiment as shown, body members 11 and 13 are L-shaped sleeve members that receive L-shaped tongue body members 12 and 14. Alternatively, each body member 11, 12, 13 and 14 may comprise one end that is a sleeve and the other end that is a tongue, or the body members 11, 12, 13 and 14 may comprises various rail-like or tongue-and-groove configurations which allow for adjustment of the overall size of the clamp 10 in the two orthogonal directions.

Figure 2:
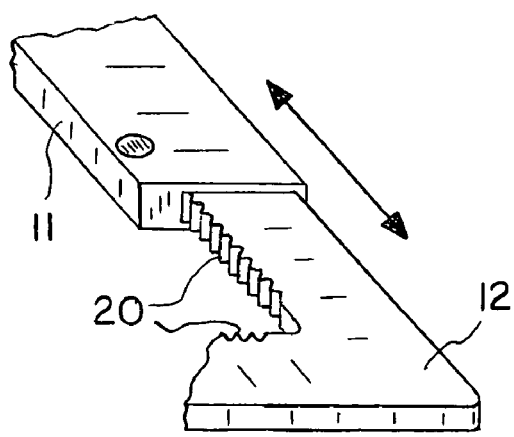
FIG. 2 is a partial view of an alternative embodiment of the sternal clamp.
Figure 3:
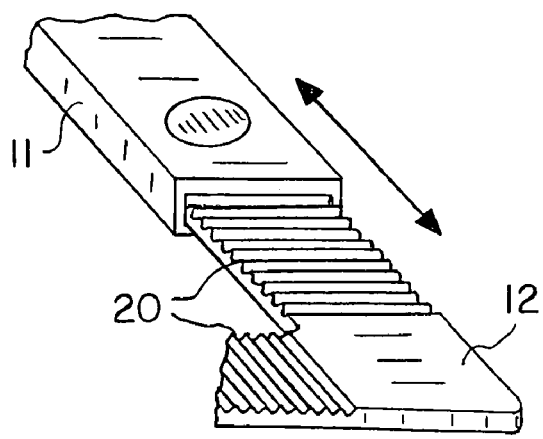
FIG. 3 is a partial view of still another embodiment of the sternal clamp.

The sternal clamp 10 further comprises means for securing the body members 11, 12, 13 and 14 in the fixed, contracted position, with the securing means preferably being releasable so that the clamp 10 can be removed as necessary. The securing means may comprise simple setscrews 19, as shown in FIG. 1, or ratchet mechanisms 20, as shown in FIGS. 2 and 3, or like systems that allow relative movement of the body members 11, 12, 13 and 14, all of which mechanisms are well known in the sternal clamp art.

It is contemplated that equivalents and substitutions for certain elements set forth above may be obvious to those of ordinary skill in the art, and therefore the true scope and definition of the invention is to be as set forth in the following claims.

We claim:

1. A sternal closure clamp comprising:
    four L-shaped body members, each of said L-shaped body members slidably inter-connected with two adjacent L-shaped body members such that the four L-shaped body members form a closed rectangular body; and
    four engagement members, each connected to one of said body members;
    whereby said body members are relatively adjustable in two orthogonal directions; and
    wherein a first free end of at least one of said L-shaped body members is slidably disposed into the mating end of the adjacent L-shaped body member, such that said first free end remains enclosed inside said adjacent L-shaped body member as the four inter-connected L-shaped body members are adjusted in either of the orthogonal directions.

2. The clamp of claim 1, wherein said engagement members are rotatably connected to said body members.

3. The clamp of claim 1, further comprising means for securing said body members in a fixed position relative to each other.

4. The clamp of claim 3, wherein said means for securing is releasable.

5. The clamp of claim 4, wherein said means for securing comprises a setscrew.

6. The clamp of claim 4, wherein said means for securing comprises a ratchet mechanism.

7. A sternal closure clamp comprising:
    four L-shaped body members slidably inter-connected to each other such that the four L-shaped body members form a closed rectangular body, two of said body members comprising sleeves to receive the free ends of the other two said body members, such that the distance between said body members can be contracted or expanded without said free ends protruding from said sleeves;
    four engagement members, each said engagement member rotatably connected to one said body member such that each body member is attached to one engagement member;
    means for securing said body members in a fixed position relative to each other.

8. The clamp of claim 7, wherein said means for securing is releasable.

9. The clamp of claim 8, wherein said means for securing comprises a setscrew.

10. The clamp of claim 8, wherein said means for securing comprises a ratchet mechanism.

11. A sternal closure clamp adapted to compress a sternum divided either longitudinally or transversely, said clamp transversely compressing the sides of sternum or longitudinally compressing pairs of ribs; said clamp comprising:
    four L-shaped body members, each of said L-shaped body members slidably inter-connected with two adjacent L-shaped body members such that the four L-shaped body members form a closed rectangular body;
    four engagement members, each said engagement member rotatably connected to one of the said body members;
    means for securing said body members in a fixed position relative to each other;
    wherein said body members are inter-connected in such a manner whereby said engagement members may be rotated to abut either pairs of ribs or the sides of the sternum; and
    wherein free ends of at least one of said L-shaped body members are slidably disposed into mating ends of the adjacent L-shaped body members, such that said free ends remain enclosed inside said mating ends of said adjacent L-shaped body members as the four inter-connected L-shaped body members are adjusted in either of the orthogonal directions.

12. The clamp of claim 11, wherein said mating ends of two of said body members comprise sleeves to receive the free ends of the other two said body members such that the distance between said body members can be contracted or expanded without said free ends protruding from said sleeves.

13. The clamp of claim 11, wherein said means for securing is releasable.

14. The clamp of claim 12, wherein said means for securing comprises a setscrew.

15. The clamp of claim 12, wherein said means for securing comprises a ratchet mechanism.

16. A sternal closure clamp comprising:
four L-shaped body members, each of said L-shaped body members having an engagement member attached thereto;
wherein each of said L-shaped body members is connected to two adjacent body members in a slidable engagement such that the four L-shaped body members interconnect to form a closed rectangular body that is slidably adjustable in two orthogonal directions; and
wherein each of said slidable engagements between adjacent body members comprises a sleeve member disposed within one L-shaped body member and receiving a tongue member disposed within the adjacent L-shaped body member such that the tip of the tongue member does not protrude from the sleeve member as the L-shaped body members are slidably adjusted.

17. The clamp of claim 16, wherein said engagement members are rotatably connected to said body members.

18. The clamp of claim 17, further comprising means for securing said body members in a fixed position relative to each other.

19. The clamp of claim 18, wherein said means for securing comprises a setscrew.

20. The clamp of claim 18, wherein said means for securing comprises a ratchet mechanism.

* * * * *